United States Patent
Badran et al.

(10) Patent No.: US 12,337,166 B2
(45) Date of Patent: Jun. 24, 2025

(54) NONINVASIVE CRANIAL NERVE THERAPY

(71) Applicant: MUSC Foundation for Research Development, Charleston, SC (US)

(72) Inventors: Bashar Badran, San Ramon, CA (US); Mark George, Sullivans Island, SC (US); Doe Jenkins, Johns Island, SC (US); Daniel Cook, Charleston, SC (US)

(73) Assignee: MUSC Foundation for Research Development, Charleston, SC (US)

( * ) Notice: Subject to any disclaimer, the term of this patent is extended or adjusted under 35 U.S.C. 154(b) by 0 days.

(21) Appl. No.: 18/059,503

(22) Filed: Nov. 29, 2022

(65) Prior Publication Data
US 2023/0191109 A1   Jun. 22, 2023

Related U.S. Application Data

(63) Continuation of application No. 17/056,506, filed as application No. PCT/US2019/033151 on May 20, 2019, now Pat. No. 11,511,105.

(60) Provisional application No. 62/757,775, filed on Nov. 9, 2018, provisional application No. 62/673,578, filed on May 18, 2018.

(51) Int. Cl.
*A61N 1/36* (2006.01)
*A61N 1/04* (2006.01)

(52) U.S. Cl.
CPC ......... *A61N 1/0452* (2013.01); *A61N 1/0456* (2013.01); *A61N 1/36031* (2017.08); *A61N 1/36034* (2017.08); *A61N 1/36036* (2017.08)

(58) Field of Classification Search
CPC ............... A61N 1/0452; A61N 1/0456; A61N 1/36031; A61N 1/36034; A61N 1/36036; A61N 1/3601; A61N 1/36025; A61N 1/0526; A61B 5/01; A61B 5/021; A61B 5/1107; A61B 5/14532; A61B 5/14542; A61B 5/318; A61B 5/369; A61B 5/389; A61B 5/4205; A61J 9/00
See application file for complete search history.

(56) References Cited

U.S. PATENT DOCUMENTS

| 8,413,502 B2 | 4/2013 | Zemel |
| 8,914,122 B2 | 12/2014 | Simon |
| 2004/0162595 A1 | 8/2004 | Foley |

(Continued)

FOREIGN PATENT DOCUMENTS

CN   105228576 A   1/2016

OTHER PUBLICATIONS

Adamkin DH. Feeding problems in the late preterm infant. Clinics in perinatology. 2006; 33: 831-7; abstract ix.

(Continued)

*Primary Examiner* — Amanda K Hulbert
*Assistant Examiner* — Natasha Patel
(74) *Attorney, Agent, or Firm* — Riverside Law LLP

(57) ABSTRACT

The present invention relates to systems for providing noninvasive cranial nerve stimulation and methods for using the same. The present invention administers therapy through electrodes that are noninvasively attached to one or more of a subject's cranial nerve. The systems can be used to enhancing rehabilitation and recovery by improving neuroplasticity and coupling muscle training with feedback.

22 Claims, 15 Drawing Sheets

(56) References Cited

U.S. PATENT DOCUMENTS

| | | |
|---|---|---|
| 2005/0216062 A1 | 9/2005 | Herbst |
| 2006/0020298 A1 | 1/2006 | Camilleri |
| 2006/0122675 A1 | 6/2006 | Libbus |
| 2007/0106338 A1 | 5/2007 | Errico |
| 2008/0039778 A1 | 2/2008 | Goldie |
| 2008/0051852 A1 | 2/2008 | Dietrich |
| 2008/0147141 A1* | 6/2008 | Testerman ......... A61N 1/36007 607/118 |
| 2008/0288016 A1* | 11/2008 | Amurthur ............ A61B 5/6826 607/44 |
| 2009/0099622 A1 | 4/2009 | Fowler |
| 2010/0305656 A1 | 12/2010 | Imran |
| 2011/0125212 A1 | 5/2011 | Tyler |
| 2012/0116182 A1 | 5/2012 | Wong |
| 2012/0203301 A1* | 8/2012 | Cameron ............... A61N 1/361 607/45 |
| 2013/0184792 A1 | 7/2013 | Simon |
| 2013/0289648 A1* | 10/2013 | Barlow ............... A61B 5/4064 607/45 |
| 2013/0296751 A1 | 11/2013 | Martin |
| 2014/0135886 A1* | 5/2014 | Cook ................. A61N 1/36025 607/136 |
| 2015/0142082 A1 | 5/2015 | Simon |
| 2015/0196247 A1 | 7/2015 | Lau |
| 2016/0074657 A1 | 3/2016 | Kwan |
| 2016/0151628 A1 | 6/2016 | Simon |
| 2016/0279021 A1 | 9/2016 | Hyde |
| 2017/0000292 A1 | 1/2017 | Park |
| 2017/0087364 A1 | 3/2017 | Cartledge |
| 2019/0151604 A1* | 5/2019 | Harper ................... A61H 23/02 |
| 2019/0222750 A1 | 7/2019 | Tsuchiya |

OTHER PUBLICATIONS

Adams-Chapman I, Bann CM, Vaucher YE, Stoll BJ, Eunice Kennedy Shriver National Institute of Child H and Human Development Neonatal Research N. Association between feeding difficulties and language delay in preterm infants using Bayley Scales of Infant Development—Third Edition. The Journal of pediatrics. 2013; 163: 680-5 e1-3.

Badran BW, Dowdle LT, Mithoefer OJ, et al. Neurophysiologic effects of transcutaneous auricular vagus nerve stimulation (taVNS) via electrical stimulation of the tragus: A concurrent taVNS/fMRI study and review. Brain Stimul. 2018; 11: 492-500.

Badran BW, Mithoefer OJ, Summer CE, et al. Short trains of transcutaneous auricular vagus nerve stimulation (taVNS) have parameter-specific effects on heart rate. Brain Stimul. 2018.

Badran, Bashar W et al. "Transcutaneous auricular vagus nerve stimulation (taVNS) for improving oromotor function in newborns." Brain stimulation vol. 11,5 (2018): 1198-1200. doi:10.1016/j.brs.2018.06.009.

Dawson J, Pierce D, Dixit A, et al. Safety, Feasibility, and Efficacy of Vagus Nerve Stimulation Paired With Upper-Limb Rehabilitation After Ischemic Stroke. Stroke. 2016; 47: 143-50.

Khodaparast N, Hays SA, Sloan AM, et al. Vagus nerve stimulation delivered during motor rehabilitation improves recovery in a rat model of stroke. Neurorehabil Neural Repair. 2014; 28: 698-706.

Khodaparast N, Kilgard MP, Casavant R, et al. Vagus Nerve Stimulation During Rehabilitative Training Improves Forelimb Recovery After Chronic Ischemic Stroke in Rats. Neurorehabilitation and neural repair. 2016; 30: 676-84.

Office Action (Non-Final Rejection) dated Feb. 16, 2022 for U.S. Appl. No. 17/056,506 (pp. 1-10).

Office Action (Notice of Allowance and Fees Due (PTOL-85)) dated Jul. 7, 2022 for U.S. Appl. No. 17/056,506 (pp. 1-2).

Porter BA, Khodaparast N, Fayyaz T, et al. Repeatedly pairing vagus nerve stimulation with a movement reorganizes primary motor cortex. Cerebral cortex. 2012; 22: 2365-74.

Pruitt DT, Schmid AN, Kim LJ, et al. Vagus Nerve Stimulation Delivered with Motor Training Enhances Recovery of Function after Traumatic Brain Injury. J Neurotrauma. 2016; 33: 871-9.

Redgrave JN, Moore L, Oyekunle T, et al. Transcutaneous Auricular Vagus Nerve Stimulation with Concurrent Upper Limb Repetitive Task Practice for Poststroke Motor Recovery: A Pilot Study. Journal of stroke and cerebrovascular diseases : the official journal of National Stroke Association. 2018.

* cited by examiner

NONINVASIVE CRANIAL NERVE THERAPY

CROSS-REFERENCE TO RELATED APPLICATIONS

This application is a continuation of U.S. patent application Ser. No. 17/056,506, filed Nov. 18, 2020, which is the U.S. national phase application filed under 35 U.S.C. § 371 claiming benefit to International Patent Application No. PCT/US19/33151, filed May 20, 2019, which is entitled to priority under 35 U.S.C. § 119 (e) to U.S. Provisional Patent Application Nos. 62/757,775, filed Nov. 9, 2018, and 62/673,578, filed May 18, 2018, the contents of which are each incorporated by reference herein in their entirety.

STATEMENT REGARDING FEDERALLY SPONSORED RESEARCH OR DEVELOPMENT

This invention was made with government support under Grant No. P2HCD086844 awarded by the National Institute of Health. The government has certain rights in the invention.

BACKGROUND OF THE INVENTION

Preterm infants and term infants who suffer hypoxic ischemic encephalopathy (HIE) are at high risk for motor problems, which primarily manifest as feeding delays during their neonatal hospital admission. Oromotor dyscoordination is very common in both groups of infants, and typically takes 3-6 weeks of working on oral feedings in the hospital before the infant may take enough breast milk or formula to sustain adequate growth for discharge. Occupational therapy usually works with infants once a day to ensure that the feeding particulars, such as nipple choice, frequency of oral feeding, do not tax infant physiology too greatly and to guide learning this motor skill. Feeding difficulty is the primary reason for delayed discharge of preterm or HIE infants. Many of these infants will not be able to master this motor skill before term age (40-42 weeks gestation) and will receive a gastrostomy tube (G-tube) for direct gastric feeding, in order that they may finally be discharged from the hospital to home. Neonatal intensive care units (NICU) place on average 40 G-tubes per year. This procedure requires general anesthesia for both insertion and eventual take down, and leaves scars in the epigastric area. The g-tube also reinforces the parental perception that their child is not normal and that he or she has a more limited developmental potential than a 'normal' child.

Even with significant brain injury, it is known that neuroplasticity in infants may lead to improved, and even near normal outcomes. This neuroplasticity involves stimulating neurogenesis and reparative inter-neuronal connections to improve motor skills in neonatal animal models and in adults after stroke. In addition, it is known that rehabilitative training may be enhanced by brain stimulation using a variety of modalities.

Feeding in neonates involves a sequence of sucking, swallowing, and breathing that requires coordination of the face, head, and neck muscles with the myelinated vagal regulation of the bronchi and the heart. In preterm neonates, the muscles needed to feed are underdeveloped, resulting in the need for OT rehabilitation to 'learn' feeding patterns. Preterm neonates' inability to feed effectively is the primary reason for prolonged hospital stays. In neonates with HIE, development of cortex and basal ganglia is interrupted, and depending on the severity, normal developmental plasticity is hindered, further contributing to their inability to feed. Both types of feeding difficulties involve complex motor learning, which requires integration of sensory and motor pathways.

Thus, there is a need in the art for improved systems and methods for administering neural stimulation for enhancing neuroplasticity and muscle training. The present invention meets this need.

SUMMARY OF THE INVENTION

In one aspect, the present invention provides a method of enhancing oromotor skills, comprising the steps of: providing a cranial nerve stimulation system comprising at least one sensing electrode and at least one stimulating electrode; securing the at least one sensing electrode adjacent to a subject's cheek or jaw muscle and the at least one stimulating electrode to a subject's cranial nerve; providing the subject with a source of food; measuring muscle activation using the at least one sensing electrode that surpasses a minimum threshold; and administering stimulation using the at least one stimulating electrode to the cranial nerve in response to the measurement of muscle activation surpassing the minimum threshold.

In one embodiment, the cranial nerve is selected from the group consisting of: the trigeminal nerve, the facial nerve, the accessory nerve, the hypoglossal nerve, the auricular branch of the vagus nerve, and the main bundle of the vagus nerve. In one embodiment, the measuring step and the administering step are repeated in a closed loop. In one embodiment, the at least one stimulating electrode is non-invasively secured to a subject's ear canal, tragus, cymba conchae, lobe, helix, anti-helix, mastoid, or neck.

In one embodiment, the minimum threshold is an absolute value selected from the group consisting of about: 0.1 µV, 0.5 µV, 1 µV, 5 µV, 10 µV, 50 µV, 100 µV, 200 µV, 300 µV, 400 V, 500 µV, 1 mV, 5 mV, 10 mV, 20 mV, 30 mV, 40 mV, or 50 mV. In one embodiment, the minimum threshold is a change from a base measurement taken at rest selected from the group consisting of about: 0.1 µV, 0.5 µV, 1 µV, 5 µV, 10 µV, 50 µV, 100 µV, 200 µV, 300 µV, 400 µV, 500 µV, 1 mV, 5 mV, 10 mV, 20 mV, 30 mV, 40 mV, or 50 mV. In one embodiment, the minimum threshold is a percentage of a maximum potential of the muscle selected from the group consisting of about: 1%, 2%, 3%, 4%, 5%, 10%, 15%, 20%, 25%, 30%, 35%, 40%, 45%, 50%, 55%, 60%, 65%, 70%, 75%, 80%, 85%, 90%, or 95%.

In one embodiment, the stimulation has an intensity selected from the group consisting of about: 0.01 mA, 0.05 mA, 0.1 mA, 0.2 mA, 0.3 mA, 0.4 mA, 0.5 mA, 0.6 mA, 0.7 mA, 0.8 mA, 0.9 mA, 1 mA, 1.5 mA, 2 mA, 2.5 mA, 3 mA, 3.5 mA, 4 mA. 4.5 mA, 5 mA. 6 mA, 7 mA, 8 mA, 9 mA, and 10 mA. In one embodiment, the stimulation has a frequency selected from the group consisting of about: 1 Hz, 2 Hz, 3 Hz, 4 Hz, 5 Hz, 6 Hz, 7 Hz, 8 Hz, 9 Hz, 10 Hz, 15 Hz, 20 Hz, 25 Hz, 30 Hz, 35 Hz, 40 Hz, 45 Hz, and 50 Hz. In one embodiment, the stimulation has a pulse width selected from the group consisting of about: 10 µs, 20 µs, 30 µs, 40 µs, 50 µs, 60 µs, 70 µs, 80 µs, 90 µs, 100 µs, 150 µs, 200 µs, 250 µs, 300 µs, 350 µs, 400 µs, 450 µs, 500 µs, 550 µs, 600 µs, 650 µs, 700 µs, 750 µs, 800 µs, 850 µs, 900 µs, 950 µs, and 1 ms. In one embodiment, the stimulation has an on duration and an off duration, each selected from the group consisting of about: 0.1 seconds, 0.5 seconds, 1.5 seconds, 2 seconds, 2.5 seconds, 3 seconds, 3.5 seconds, 4 seconds, 4.5 seconds, 5 seconds, 10 seconds, 20 seconds, 30 seconds, 40 seconds, 50 seconds, 1 minute, 2 minutes, 3 minutes, 4 minutes, 5 minutes, 10 minutes, 15 minutes, 20 minutes, 30 minutes, 40 minutes, 45 minutes, 50 minutes, and 1 hour.

In another aspect, the present invention provides a cranial nerve stimulation system, comprising: at least one sensing electrode configured to attach adjacent to at least one muscle; and at least one stimulating electrode configured to attach adjacent to a cranial nerve; wherein the at least one stimulating electrode is electrically linked to the at least one sensing electrode such that the at least one stimulating electrode is activated to stimulate the cranial nerve when the at least one sensing electrode measures electrical energy in the at least one muscle that passes a minimum threshold.

In one embodiment, the at least one cranial nerve is selected from the group consisting of: the trigeminal nerve, the facial nerve, the accessory nerve, the hypoglossal nerve, the auricular branch of the vagus nerve, and the main bundle of the vagus nerve.

In one embodiment, the system further comprises a power source, a transmitter, and a processor communicatively connected to a non-transitory computer-readable memory with instructions store thereon, which when executed by the processor, initiates a closed-loop synchronization between activation and deactivation of the at least one stimulating electrode with the at least one sensing electrode measuring electrical energy that passes a minimum threshold.

In one embodiment, the system further comprises a feeding bottle comprising at least one sensor, a power source, and a transmitter. In one embodiment, the at least one sensor is selected from the group consisting of: a flow sensor, a pressure sensor, a suction sensor, a gyroscope, an accelerometer, a temperature sensor, and a volume sensor. In one embodiment, the system further comprises a power source, a transmitter, and a processor communicatively connected to a non-transitory computer-readable memory with instructions store thereon, which when executed by the processor, synchronize activation and deactivation of the at least one stimulating electrode with the at least one sensor sensing feeding from the bottle and cessation of feeding from the bottle.

In another aspect, the present invention provides a method of enhancing muscle rehabilitation, comprising the steps of: providing a cranial nerve stimulation system comprising at least one sensing electrode and at least one stimulating electrode; securing the at least one sensing electrode adjacent to a subject's muscle group of interest and the at least one stimulating electrode to a subject's cranial nerve; measuring muscle group activation using the at least one sensing electrode that surpasses a minimum threshold; and administering stimulation using the at least one stimulating electrode to the cranial nerve in response to the measurement of muscle group activation surpassing the minimum threshold.

In one embodiment, the cranial nerve is selected from the group consisting of: the trigeminal nerve, the facial nerve, the accessory nerve, the hypoglossal nerve, the auricular branch of the vagus nerve, and the main bundle of the vagus nerve. In one embodiment, the measuring step and the administering step are repeated in a closed loop.

BRIEF DESCRIPTION OF THE DRAWINGS

The following detailed description of exemplary embodiments of the invention will be better understood when read in conjunction with the appended drawings. It should be understood, however, that the invention is not limited to the precise arrangements and instrumentalities of the embodiments shown in the drawings.

FIG. 13A shows fractional anisotropy (FA) change per week between responders (full feed) and non-responders (G-tube) in the Left External Capsule and Right Corpus Callosum, two white matter regions of interest important in motor integration. FIG. 13B shows axial kurtosis ($K_{\parallel}$) change per week between responders (full feed) and non-responders (G-tube) in Left Posterior Thalamic Radiations (PTR) and Right Inferior Front-Occipital Fasciculus (IFOF), two white matter regions of interest important in sensorimotor integration.

DETAILED DESCRIPTION

Figure 1A:
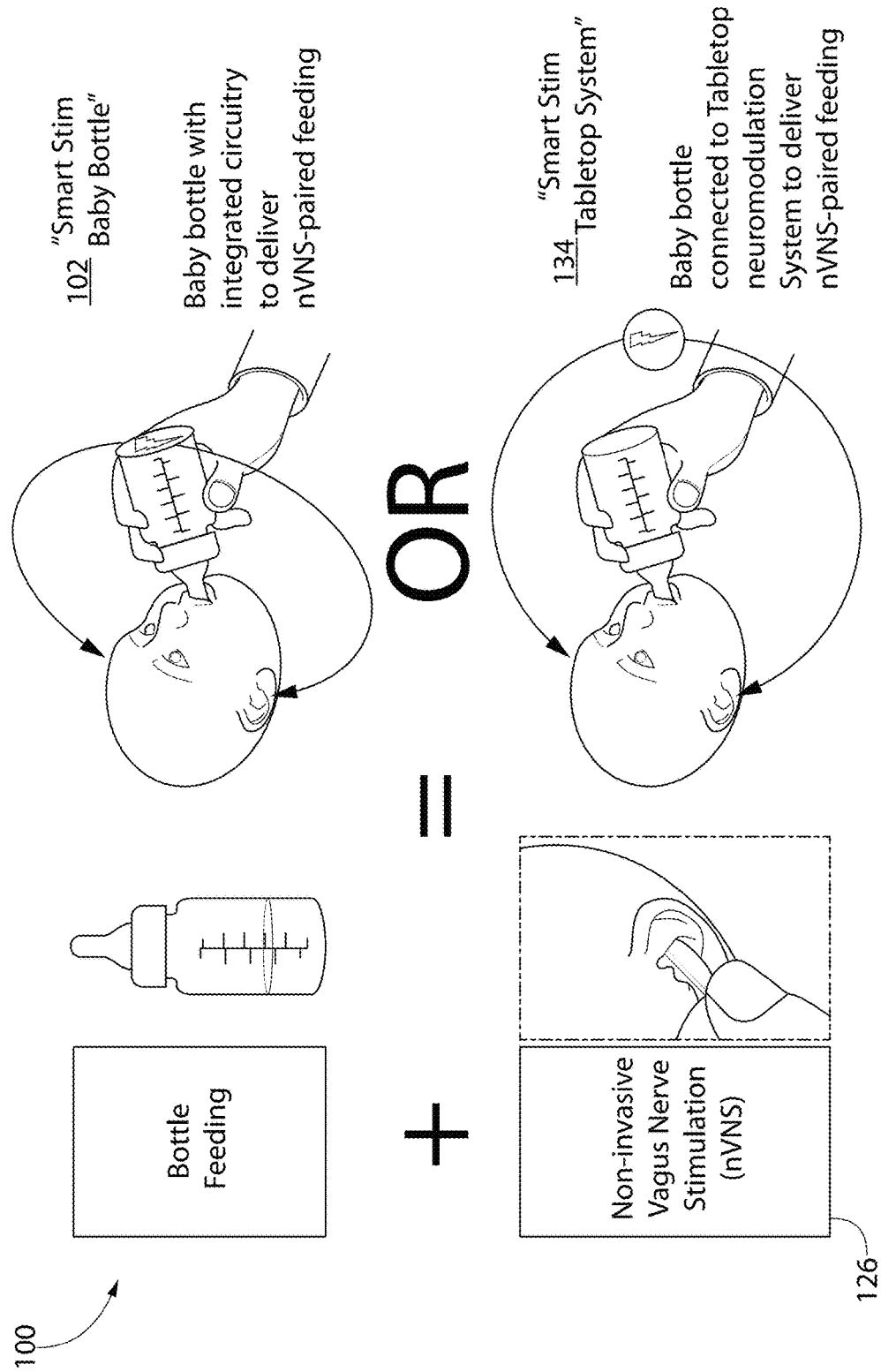
FIG. 1A and FIG. 1B depict diagrams showing exemplary systems for pairing noninvasive cranial nerve stimulation with neonate feeding.

It is to be understood that the figures and descriptions of the present invention have been simplified to illustrate elements that are relevant for a clear understanding of the present invention, while eliminating, for the purpose of clarity, many other elements typically found in the art. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined elsewhere, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of +20%, +10%, +5%, +1%, and +0.1% from the specified value, as such variations are appropriate.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6, and any whole and partial increments there between. This applies regardless of the breadth of the range.

Cranial Nerve Stimulation Systems

The present invention is based in part on systems for providing noninvasive cranial nerve stimulation. The systems administer therapy through electrodes that are noninvasively attached to one or more of a subject's cranial nerve. The systems can be used to enhancing rehabilitation and recovery by improving neuroplasticity and coupling muscle training with feedback.

Stimulation can be noninvasively administered to any suitable cranial nerve. Non-limiting examples include the trigeminal nerve, the facial nerve, the accessory nerve, the hypoglossal nerve, the auricular branch of the vagus nerve, the main bundle of the vagus nerve, and the like. The auricular branch of the vagus nerve can be accessed in a variety of ways, including but not limited to the ear canal, the tragus, the cymba conchae, the outer ear, the mastoid, and combinations thereof. The main bundle of the vagus nerve can be accessed at any suitable location along the neck. In various embodiments, the stimulation is administered transcutaneously. Stimulation can be administered using one or more electrodes secured adjacent to a cranial nerve in any suitable manner, including but not limited to using an adhesive, a clip, a patch, an ear plug, a head band, a neck brace, a collar, a head covering, and the like.

In some embodiments, the present invention provides therapeutic tools aimed at improving and accelerating learned feeding behavior in neonates. The systems provided change the way rehabilitation is conducted for preterm neonates, resulting in earlier discharge, lower hospital costs, improved parental perception of the developmental potential of their infant, and reduces stress and improves bonding with parents, both in and out of the hospital. The systems can serve as a take-home feeding aid for convalescing critically ill infants who have missed the developmental window to master the feeding skill, and for infants with congenital syndromes that make oral feeding challenging.

Treating oromotor difficulties during the learned task of feeding with noninvasive brain stimulation that promotes plasticity, poses a highly novel application of transcutaneous auricular vagus nerve stimulation (taVNS). The major premise is that in babies at high risk for motor problems, simultaneously delivered brain stimulation via taVNS will boost motor cortical plasticity involved in a learned feeding task, leading to better feeding. There may be a synergistic effect of surgically implanted VNS when combined with a paired stimulus that directs plastic changes to occur in the cortex. This invention utilizes novel forms of noninvasive vagus nerve stimulation (nVNS) (rather than surgically implanted) paired with feeding to accelerate and enhance the learning of feeding in neonates.

Figure 1B:
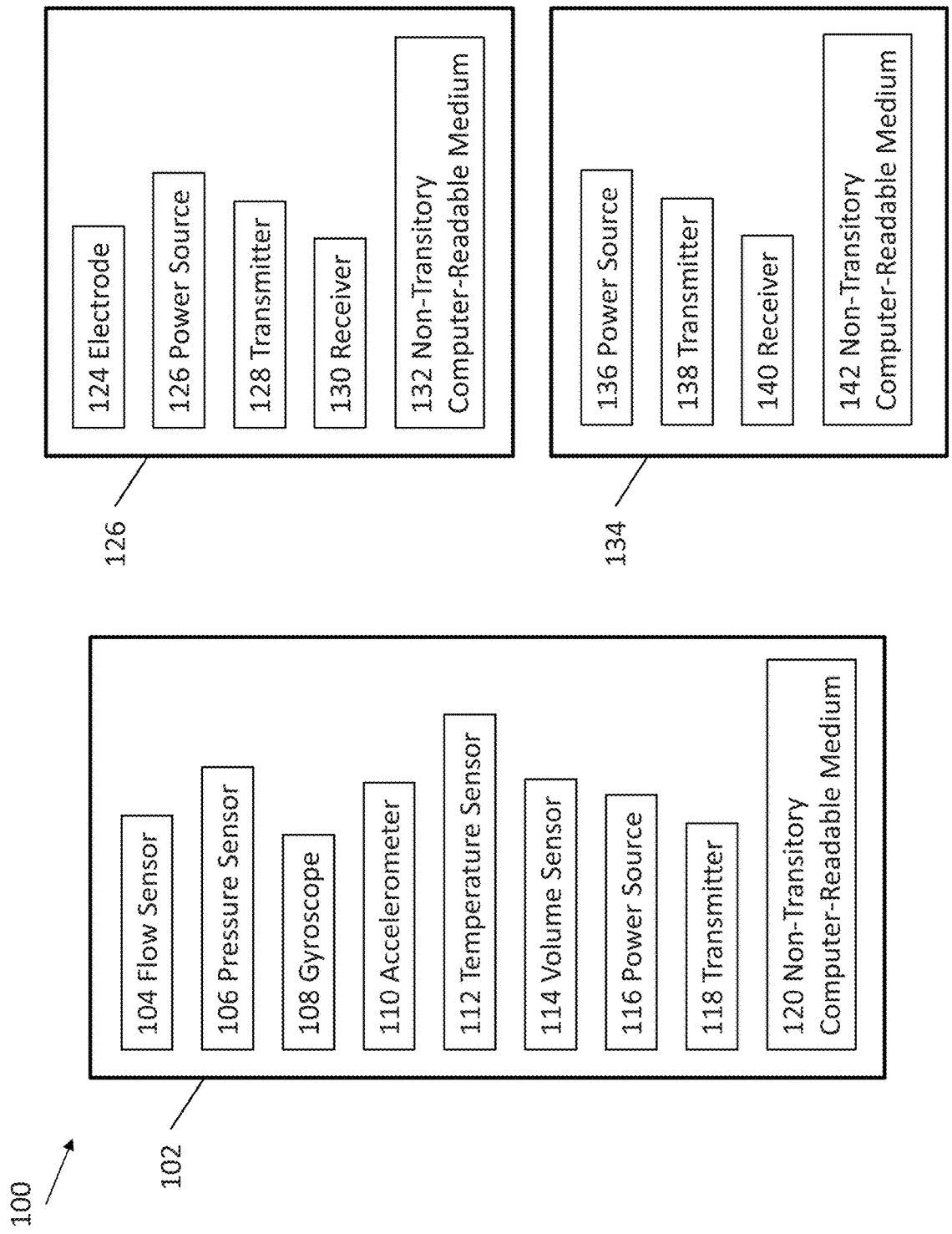

Referring now to FIG. 1A and FIG. 1B, an exemplary system 100 is depicted. In various embodiments, system 100 comprises several components that can be used alone or in combination to couple cranial nerve stimulation with feedback to train feeding behavior in infants. For example, in some embodiments system 100 comprises bottle 102, wearable 122, and computer platform 134.

Bottle 102 can comprise any desired feeding bottle with reservoir connected to a mouthpiece having a nipple or other aperture suitable for engaging an infant's mouth typically used for feeding infants, with the further addition of at least one flow sensor 104, pressure sensor 106, gyroscope 108, accelerometer 110, temperature sensor 112, volume sensor 114, and combinations thereof. The at least one flow sensor 104 and pressure sensor 106 can be used to detect and measure the timing and amount of food obtained by an infant during a feeding session. The at least one gyroscope 108 and accelerometer 110 can be used to detect and measure the position of bottle 102 and monitor feeding behavior over time as a function of the movement of bottle 102. The at least one temperature sensor 112 can be used to monitor the temperature of bottle 102 to indicate whether the contents are at a suitable temperature, or whether the contents are too cold or too hot for consumption. The at least one volume sensor 114 can be used to detect and measure the amount of food remaining in bottle 102. Any suitable volume sensor 114 can be used, including float sensors, ultrasonic level sensors, laser level sensors, and the like. Additional sensors are also contemplated, such as suction sensors, blood pressure sensors, pulse oximetry sensors, glucose sensors, and the like. In some embodiments, bottle 102 can be powered by a power source 116 (such as a battery or an electrical plug). In some embodiments, bottle 102 can further include a wired or wireless transmitter 118 for transmitting data collected by the various sensors, and a non-transitory computer-readable medium 120 connected to a processor to store data collected by the various sensors.

Wearable 122 comprises an assortment of sensing and stimulating components, and can be in the form of an article of clothing or harness that can be worn by a subject to position the components adjacent to regions of sensing and stimulating interest. Wearable 122 comprises at least one electrode 124. The at least one electrode 124 includes stimulating electrodes and can also include sensing electrodes. Stimulating electrodes are configured to administer electrical stimulation, while sensing electrodes are configured to measure a physiological response. For example, sensing electrodes can include electrocardiogramyography electrodes, electroencephalography electrodes, and the like. In some embodiments, the stimulating electrodes are electrically linked to the sensing electrodes. In various embodiments, wearable 122 can further include one or more additional sensors, such as temperature sensors, blood pressure sensors, pulse oximetry sensors, glucose sensors, and the like. Wearable 122 can further be powered by a power source 126 (such as a battery or an electrical plug). In some embodiments wearable 122 can further include a wired or wireless transmitter 128 for transmitting data collected by the various electrodes and sensors, a wired or wireless receiver 130 for receiving instructions for activating stimulating electrodes, and a non-transitory computer-readable medium 132 connected to a processor to store data collected by the various electrodes and sensors.

Computer platform 134 comprises a wired or wireless transmitter 138 for transmitting instructions to wearable 122, a wired or wireless receiver 140 to collected data from bottle 102, wearable 122, or both, a non-transitory computer-readable medium 142 connected to a processor to store instructions and collected data, and can be powered by a power source 136 (such as a battery or an electrical plug).

Figure 2:
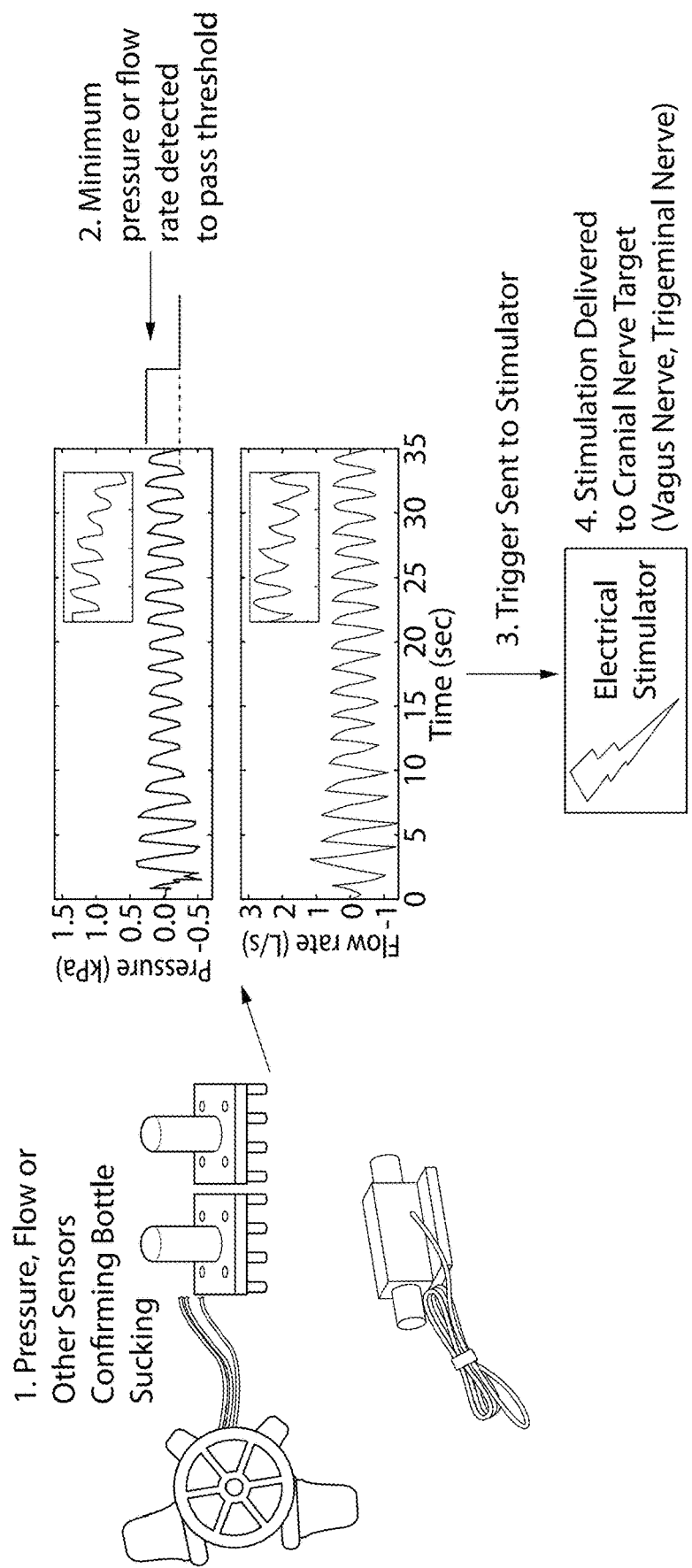
FIG. 2 depicts a diagram showing an exemplary system for triggering cranial nerve stimulation in neonate feeding.

As described above, the various components of system 100 can be used alone or in combination to couple cranial nerve stimulation with feedback. In a non-limiting first example, bottle 102 is coupled with wearable 122. Bottle 102 can communicate with wearable 122 by way of transmitter 118 to receiver 130 that bottle 102 is in position for feeding. As shown in FIG. 2, bottle 102 can sense a minimum change in volume, flow, and/or pressure that passes a threshold to initiate a trigger. Bottle 102 communicates to wearable 122 to supplement feeding behavior by activating an electrode 124 adjacent to a cranial nerve, thereby stimulating the cranial nerve. Feeding behavior can be monitored and further verified by bottle 102. Feeding behavior can also be monitored and verified by an electrode 124 sensing cheek and jaw muscle activation. Feeding can continue by timing and synchronizing sensing of feeding initiation from bottle 102 and stimulation from wearable 122.

In a non-limiting second example, wearable 122 can be used alone as a closed loop system. A sensing electrode 124 adjacent to one or more cheek and jaw muscles can be used to sense feeding initiation through a minimum change in muscle activation that passes a threshold to initiate a trigger. In response to the trigger, wearable 122 supplements feeding behavior by activating a stimulating electrode 124 adjacent to a cranial nerve. Feeding can continue by timing and synchronizing sensing of feeding initiation from a sensing electrode 124 and stimulation from a stimulating electrode 124. In this manner, wearable 122 functions as a closed-loop system between sensing a minimum cheek and jaw muscle activation indicating feeding initiation and administering cranial nerve stimulation.

Computer platform 134 can be used to supplement communication between bottle 102 and wearable 122. Computer platform 134 can also be used to facilitate operation, monitoring, and data collection/storage for bottle 102, wearable 122, or both. In some embodiments, computer platform 134 can be used to adjust the timing and intensity of electrode stimulation in wearable 122 according to data received from bottle 102, wearable 122, or both. In some embodiments, the timing and intensity of electrode stimulation in wearable 122 is adjusted automatically to maintain measurable parameters within thresholds set by computer platform 134. Measurable parameters include but are not limited to heart rate, blood pressure, muscle activation rate, neural patterns, bottle volume, bottle position, and the like. In some aspects of the present invention, software executing the instructions provided herein may be stored on a non-transitory computer-readable medium, wherein the software performs some or all of the steps of the present invention when executed on a processor.

Aspects of the invention relate to algorithms executed in computer software. Though certain embodiments may be described as written in particular programming languages, or executed on particular operating systems or computing platforms, it is understood that the system and method of the present invention is not limited to any particular computing language, platform, or combination thereof. Software executing the algorithms described herein may be written in any programming language known in the art, compiled or interpreted, including but not limited to C, C++, C#, Objective-C, Java, JavaScript, Python, PHP, Perl, Ruby, or Visual Basic. It is further understood that elements of the present invention may be executed on any acceptable computing platform, including but not limited to a server, a cloud instance, a workstation, a thin client, a mobile device, an embedded microcontroller, a television, or any other suitable computing device known in the art.

Parts of this invention are described as software running on a computing device. Though software described herein may be disclosed as operating on one particular computing device (e.g. a dedicated server or a workstation), it is understood in the art that software is intrinsically portable and that most software running on a dedicated server may also be run, for the purposes of the present invention, on any of a wide range of devices including desktop or mobile devices, laptops, tablets, smartphones, watches, wearable electronics or other wireless digital/cellular phones, televisions, cloud instances, embedded microcontrollers, thin client devices, or any other suitable computing device known in the art.

Similarly, parts of this invention are described as communicating over a variety of wireless or wired computer networks. For the purposes of this invention, the words "network", "networked", and "networking" are understood to encompass wired Ethernet, fiber optic connections, wireless connections including any of the various 802.11 standards, cellular WAN infrastructures such as 3G or 4G/LTE networks, Bluetooth®, Bluetooth® Low Energy (BLE) or Zigbee® communication links, or any other method by which one electronic device is capable of communicating with another. In some embodiments, elements of the networked portion of the invention may be implemented over a Virtual Private Network (VPN).

It should be understood that the components of system 100 are not limited to use in training feeding behavior and can be used to enhance infant development in a variety of manners. In some embodiments, cranial nerve stimulation is effective in increasing brain white matter integrity and inter-regional communication among the various regions of the brain. In some embodiments, cranial nerve stimulation is effective in enhancing motor function, such that activities including head lifting, rolling, sitting up, gripping, lifting, throwing, crawling, walking, climbing, and descending can be trained and improved. In some embodiments, cranial nerve stimulation is effective in modulating behavior. Behavior modulation can include positive reinforcement for good behavior, negative reinforcement for bad behavior, and the reduction or treatment of neurological and psychological disorders or injury.

Figure 3:
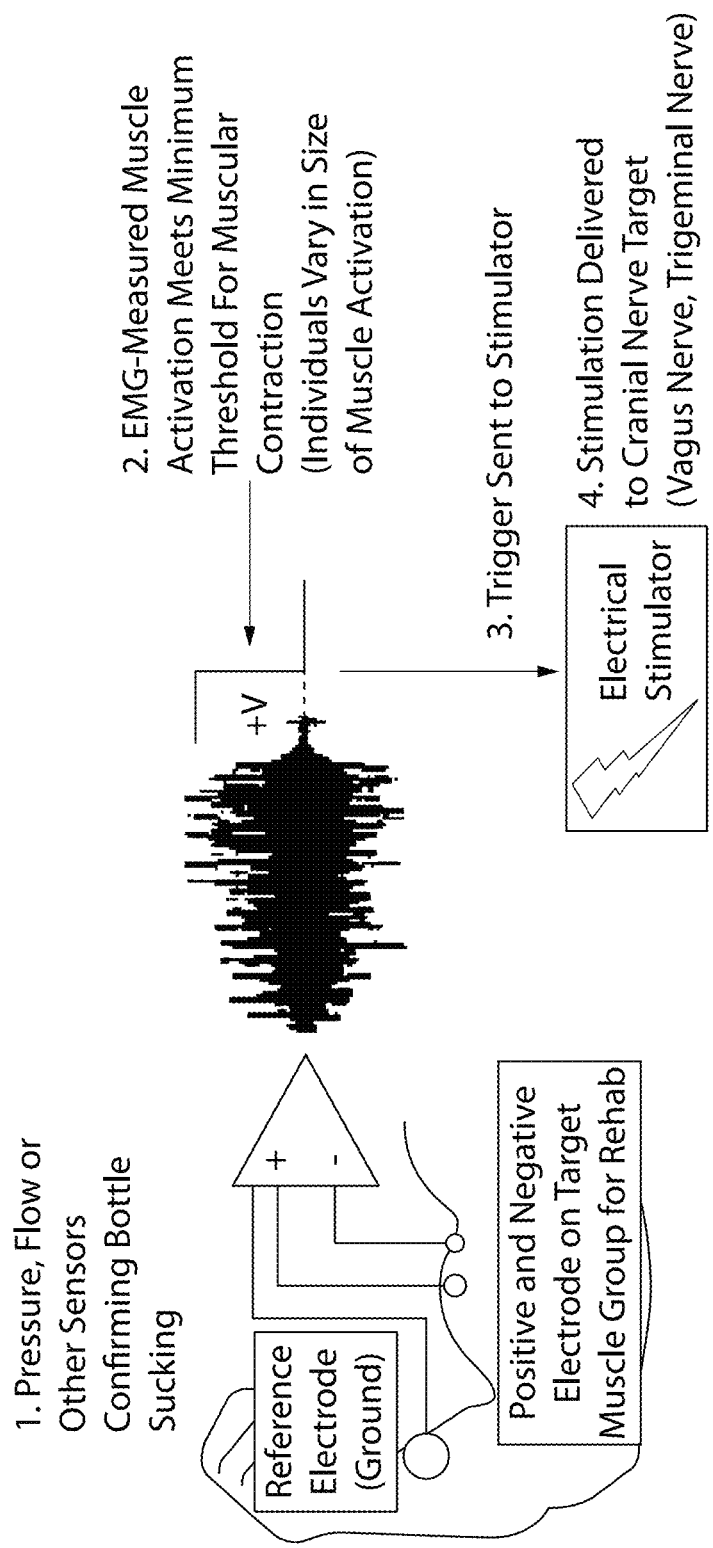
FIG. 3 depicts a diagram showing an exemplary system for triggering cranial nerve stimulation in muscle rehabilitation.

It should be understood that the components of system 100 are not limited to use in infants and can be used in children, adults, and the elderly. In various embodiments, the components of system 100 are further applicable to animals, including mammals, reptiles, birds, fish, and the like. In some embodiments, cranial nerve stimulation is effective in treating muscle-related disorders and rehabilitation, such as post-stroke upper and lower motor limb rehab paradigms, wherein muscle groups involved in specific rehabilitation paradigms are targeted. For example, referring now to FIG. 3, components of system 100 (such as a sensing electrode 124 on wearable 122) can measure muscle activation in one or more muscle groups of interest that passes a minimum threshold to initiate a trigger. Wearable 122 can supplement muscle activation by activating a stimulating electrode 124 adjacent to a cranial nerve, thereby stimulating the cranial nerve. Further activation of the one or more muscle groups of interest can be monitored and verified by a sensing electrode 124. Muscle activation can continue by timing and synchronizing sensing of muscle activation initiation from a sensing electrode 124 and stimulation from a stimulating electrode 124, such as in a closed loop system. In some embodiments, cranial nerve stimulation is effective in modulating muscular or neural diseases or disorders, including but not limited to Parkinson's disease, dyskinesia, dystonia, and the like.

Cranial Nerve Stimulation Methods

The present invention is also based in part on methods for administering noninvasive cranial nerve stimulation. As described elsewhere herein, the methods are effective in enhancing rehabilitation and recovery by improving neuroplasticity and coupling muscle training with feedback.

Figure 4:
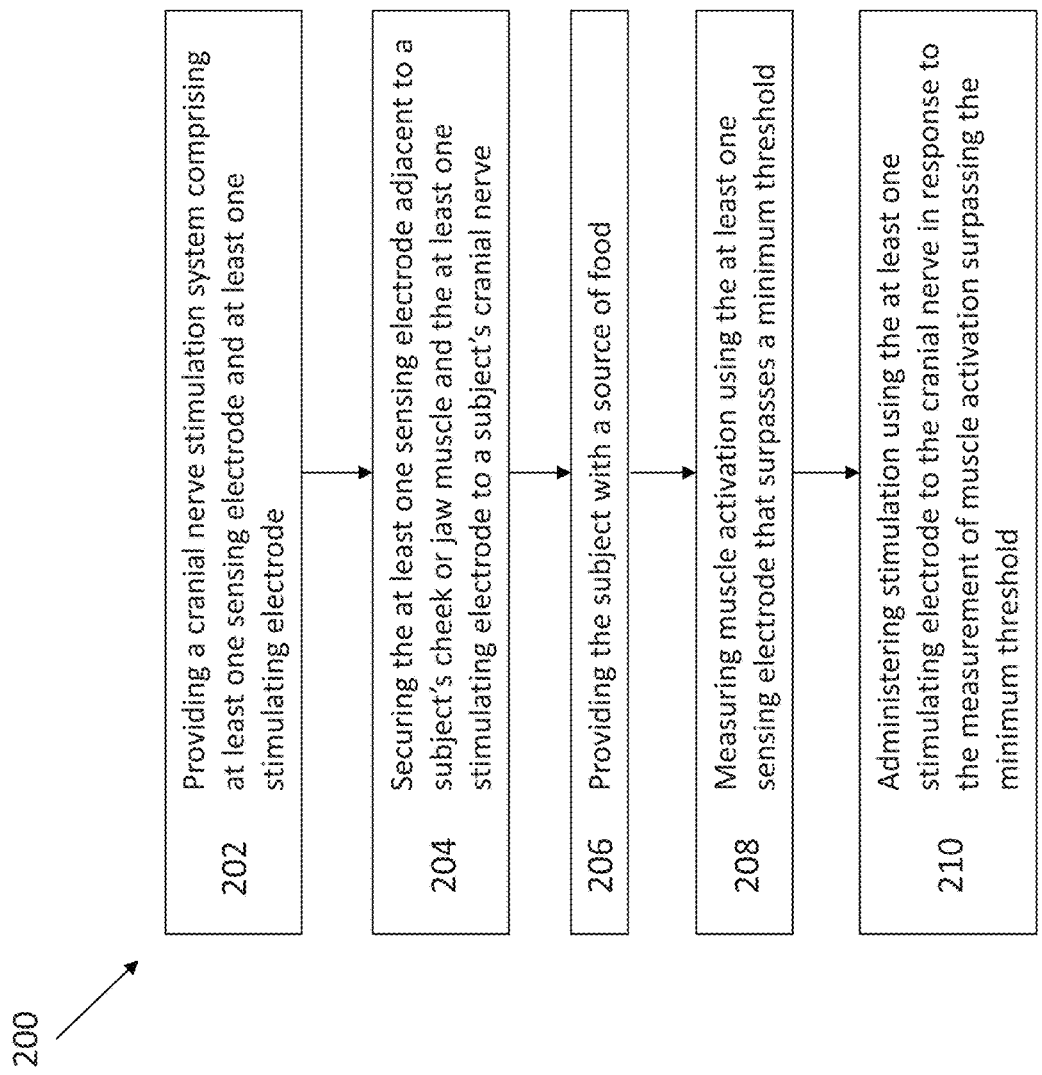
FIG. 4 depicts a flowchart for an exemplary method of training neonate feeding.

In some embodiments, the methods relate to enhancing oromotor skills. Referring now to FIG. 4, an exemplary method 200 is depicted. Method 200 begins with step 202, wherein a cranial nerve stimulation system is provided, the system comprising at least one sensing electrode and at least one stimulating electrode. In step 204, the at least one sensing electrode is noninvasively secured adjacent to a subject's cheek or jaw muscle, and the at least one stimulating electrode is noninvasively secured adjacent to a subject's cranial nerve. In step 206, the subject is provided with a source of food. In step 208, muscle activation is measured using the at least one sensing electrode that surpasses a minimum threshold, indicating feeding initiation. In step 210, stimulation is administered using the at least one stimulating electrode to the cranial nerve in response to the measurement of muscle activation surpassing the minimum threshold.

In some embodiments, the subject is an infant, and the oromotor skills relate to suckling. In various embodiments, the cranial nerve can be selected from the group consisting of the trigeminal nerve, the facial nerve, the accessory nerve, the hypoglossal nerve, the auricular branch of the vagus nerve, the main bundle of the vagus nerve, and the like. In various embodiments, the electrodes are noninvasively secured using an adhesive, a clip, a patch, an ear plug, a head band, a neck brace, a collar, a head covering, and the like. In some embodiments, the steps are performed in the recited order. In various embodiments, step 208 and step 210 are repeated in a closed loop system. In some embodiments, the methods relate to muscle rehabilitation.

Figure 5:
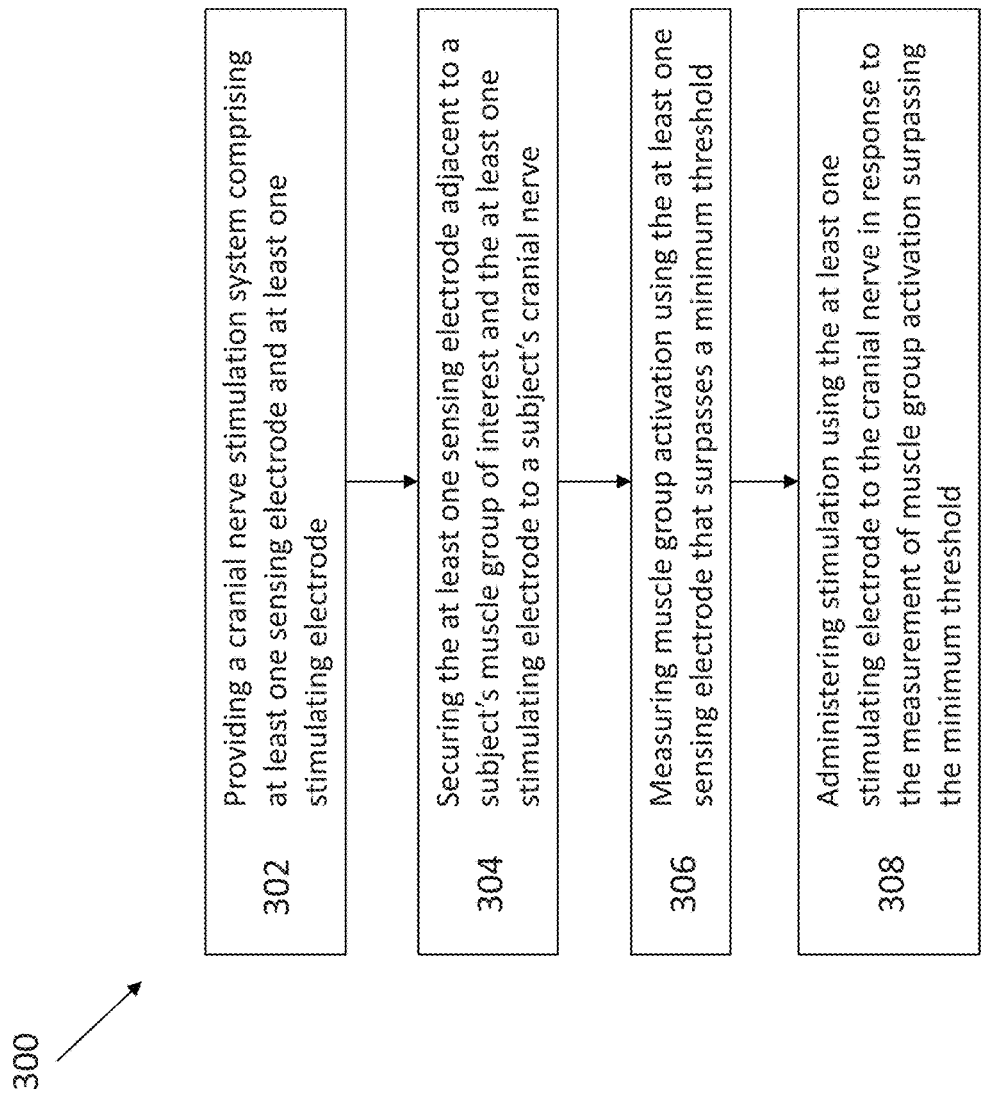
FIG. 5 depicts a flowchart for an exemplary method of training muscle rehabilitation.

Referring now to FIG. 5, an exemplary method 300 is depicted. Method 300 begins with step 302, wherein a cranial nerve stimulation system is provided, the system comprising at least one sensing electrode and at least one stimulating electrode. In step 304, the at least one sensing electrode is noninvasively secured adjacent to a subject's muscle group of interest, and the at least one stimulating electrode is noninvasively secured adjacent to a subject's cranial nerve. In step 306, muscle group activation is measured using the at least one sensing electrode that surpasses a minimum threshold. In step 308, stimulation is administered using the at least one stimulating electrode to the cranial nerve in response to the measurement of muscle group activation surpassing the minimum threshold.

In various embodiments, the cranial nerve can be selected from the group consisting of the trigeminal nerve, the facial nerve, the accessory nerve, the hypoglossal nerve, the auricular branch of the vagus nerve, the main bundle of the vagus nerve, and the like. In various embodiments, the electrodes are noninvasively secured using an adhesive, a clip, a patch, an ear plug, a head band, an arm band, a brace, a collar, a wrapping, and the like. In some embodiments, the steps are performed in the recited order. In various embodiments, step 306 and step 308 are repeated in a closed loop system.

In various embodiments, the methods of the present invention select certain minimum thresholds of muscle activation. In some embodiments, the methods select for a minimum threshold of muscle activation that is determined by an absolute measurement. For example, the minimum threshold of muscle activation can be selected from an absolute value of about 0.1 μV, 0.5 μV, 1 μV, 5 μV, 10 μV, 50 μV, 100 μV, 200 μV, 300 μV, 400 μV, 500 μV, 1 mV, 5 mV, 10 mV, 20 mV, 30 mV, 40 mV, or 50 mV. In some embodiments, the methods select for a minimum threshold of muscle activation that is determined by a change from a base measurement taken at rest. For example, the minimum threshold of muscle activation can be selected from an increase or decrease of about 0.1 μV, 0.5 μV, 1 μV, 5 μV, 10 μV, 50 μV, 100 μV, 200 μV, 300 μV, 400 μV, 500 μV, 1 mV, 5 mV, 10 mV, 20 mV, 30 mV, 40 mV, or 50 mV. In some embodiments, the methods select for a minimum threshold of muscle activation that is determined by a percentage of a typical maximum potential of the muscle. For example, the minimum threshold of muscle activation can be selected from about 1%, 2%, 3%, 4%, 5%, 10%, 15%, 20%, 25%, 30%, 35%, 40%, 45%, 50%, 55%, 60%, 65%, 70%, 75%, 80%, 85%, 90%, or 95% of the typical maximum potential of the muscle.

In various embodiments, the methods of the present invention select certain parameters for cranial nerve stimulation. In some embodiments, the methods select for an intensity of stimulation. For example, the intensity of stimulation can be selected from about 0.01 mA, 0.05 mA, 0.1 mA, 0.2 mA, 0.3 mA, 0.4 mA, 0.5 mA, 0.6 mA, 0.7 mA, 0.8 mA, 0.9 mA, 1 mA, 1.5 mA, 2 mA, 2.5 mA, 3 mA, 3.5 mA, 4 mA, 4.5 mA, 5 mA, 6 mA, 7 mA, 8 mA, 9 mA, or 10 mA. In some embodiments the methods select for a frequency of stimulation. For example, the frequency of stimulation can be selected from about 1 Hz, 2 Hz, 3 Hz, 4 Hz, 5 Hz, 6 Hz, 7 Hz, 8 Hz, 9 Hz, 10 Hz, 15 Hz, 20 Hz, 25 Hz, 30 Hz, 35 Hz, 40 Hz, 45 Hz, or 50 Hz. In some embodiments, the methods select for a pulse width of stimulation. For example, the pulse width of stimulation can be selected from about 10 μs, 20 μs, 30 μs, 40 μs, 50 μs, 60 μs, 70 μs, 80 μs, 90 μs, 100 μs, 150 μs, 200 μs, 250 μs, 300 μs, 350 μs, 400 μs, 450 μs, 500 μs, 550 μs, 600 μs, 650 μs, 700 μs, 750 μs, 800 μs, 850 μs, 900 μs, 950 μs, or 1 ms. In some embodiments, the methods select for a duration of stimulation on and off periods. For example, the duration of stimulation on and off periods can be selected from about 0.1 seconds, 0.5 seconds, 1.5 seconds, 2 seconds, 2.5 seconds, 3 seconds, 3.5 seconds, 4 seconds, 4.5 seconds, 5 seconds, 10 seconds, 20 seconds, 30 seconds, 40 seconds, 50 seconds, 1 minute, 2 minutes, 3 minutes, 4 minutes, 5 minutes, 10 minutes, 15 minutes, 20 minutes, 30 minutes, 40 minutes, 45 minutes, 50 minutes, and 1 hour. The on and off periods can have the same duration or different durations.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out exemplary embodiments of the present invention, and are not to be construed as limiting in any way the remainder of the disclosure.

Example 1: How to Measure a Baby's Suck? Closing the Loop on Transcutaneous Auricular Vagus Nerve Stimulation (taVNS) to Enhance Oromotor Development of Impaired Infants: which Electrode is Best?

Feeding difficulty due to oromotor dyscoordination is a primary concern for infants who are born preterm or suffer hypoxic ischemic encephalopathy (HIE). Vagal Nerve Stimulation (VNS) can increase neural plasticity, and when paired with rehabilitation, can enhance motor learning. Recently, it was demonstrated that non-invasive VNS can be accomplished via electrical stimulation of the auricular branch of the vagus nerve using a new method called transcutaneous auricular vagus nerve stimulation (taVNS). The goal of the present study is to develop a closed-loop automatic system that pairs taVNS with muscle activation from sucking, using electromyography (EMG) as a trigger. This system may allow better suck and stimulus pairing that is also less labor-intensive.

Figure 6:
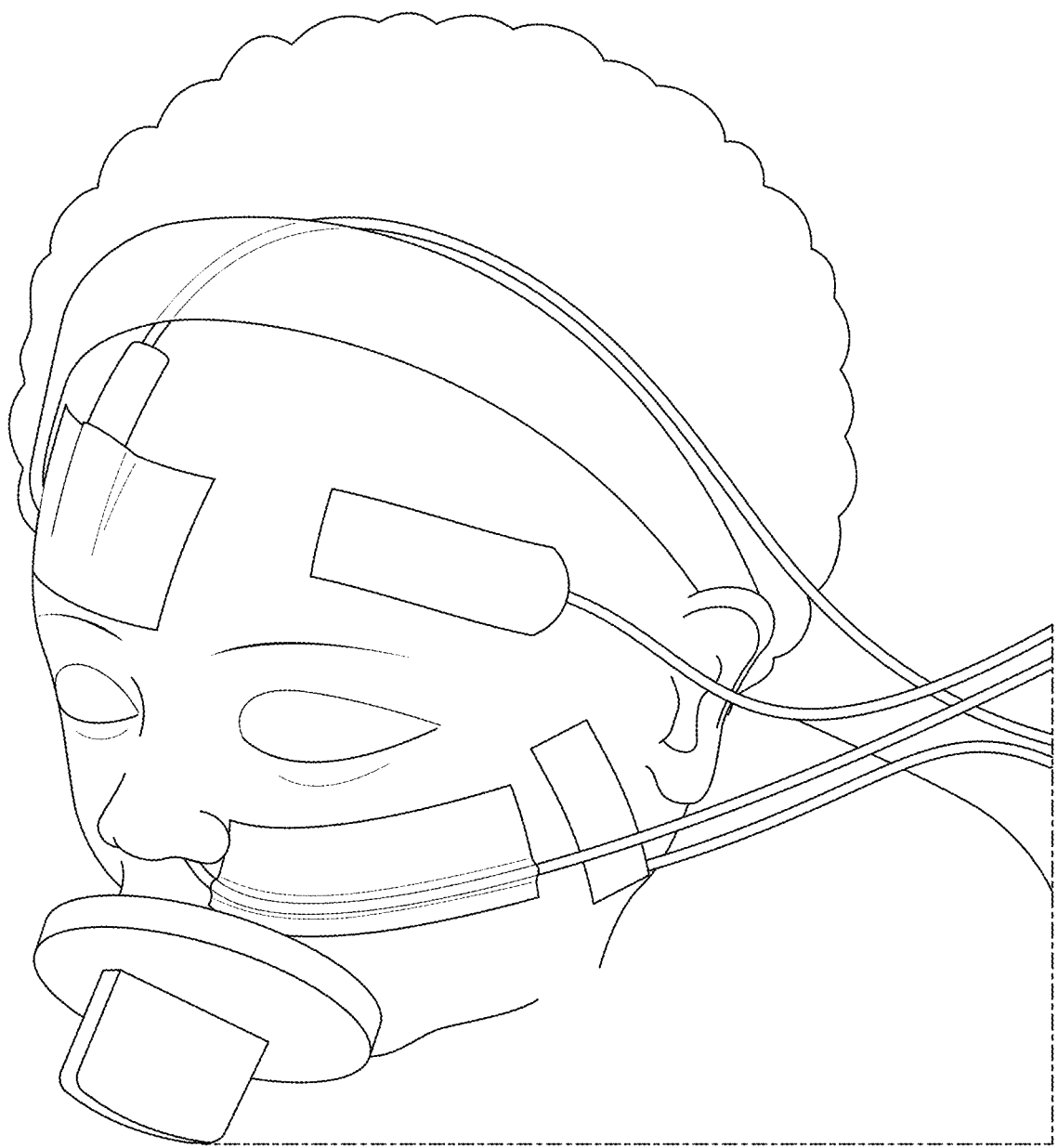
FIG. 6 depicts exemplary electromyography electrode placement for muscle activation detection and stimulation in training neonate feeding behavior.
Figure 7:
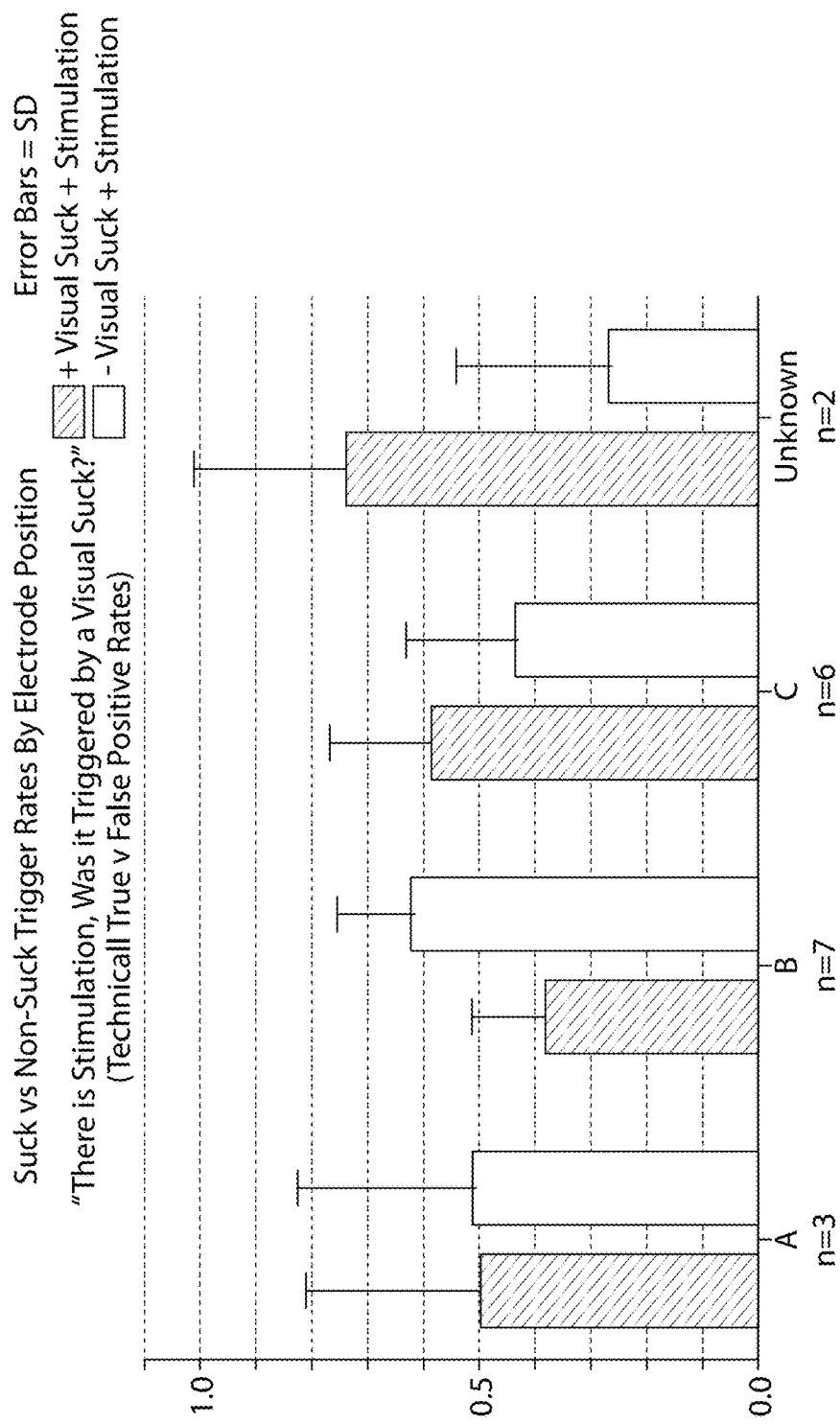
FIG. 7 depicts the results of experiments investigating optimal electrode placement that delivers the most reliable stimulation trigger induced by a visual suck in neonate feeding.
Figure 8:
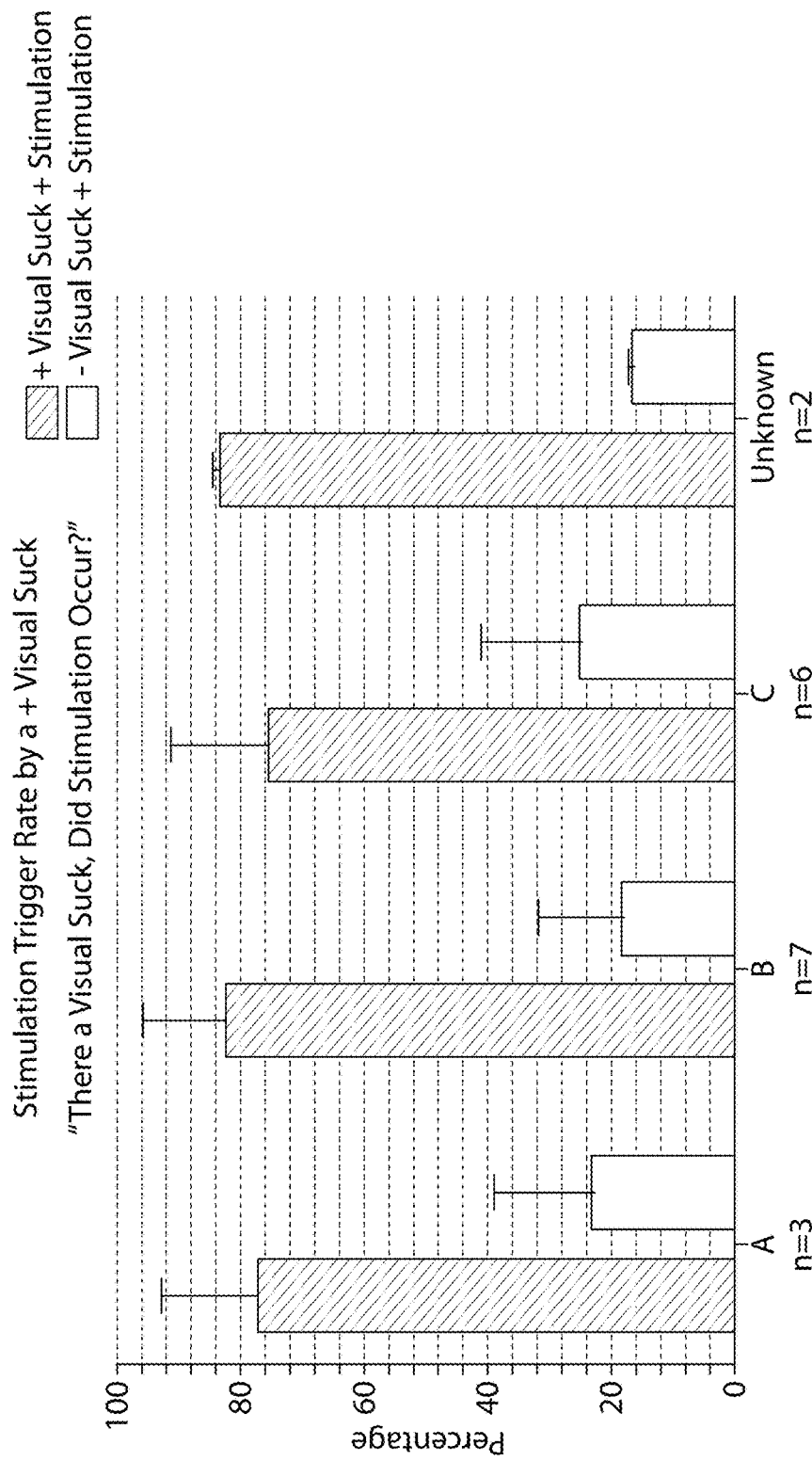
FIG. 8 depicts the results of experiments investigating optimal electrode placement that delivers the highest rate of stimulation when a visual suck is recorded in neonate feeding.

These investigations were designed to test the best location for reference electrode placement and the fidelity of stimulation paired with sucking. Three different EMG electrode placements (A, B, C) were compared to optimize the specificity and sensitivity of the automated system in 2 pre-term neonates enrolled in a larger pilot trial (example shown in FIG. 6). Triggered stimulation was delivered using a left ear electrode at 0.1 mA below perceptual threshold, 25 Hz frequency, 500 μs pulse width, for a 3.5 second train. The primary outcomes of this study were specificity (stimulations correctly paired to a visual suck, FIG. 7) and sensitivity (visual sucks that triggered or occurred during stimulation, FIG. 8).

Locations A, B, and C had a mean specificity of 49.3+31.8 (n=3), 37.9=13.4 (n=7), and 58.3=18.5 (n=6), respectfully. Locations A, B, and C had a mean sensitivity of 77±15.9 (n=3), 82±13.8 (n=7), and 75.2±16.2 (n=6), respectively. Electrode placement C was feasible and better tolerated. The placement produced the highest average (60%) rate of stimulation induced by a real visual suck while minimizing stimulation triggered by non-visual suck (40%). All placements seemed to perform equally at a rate of about 77-81% triggers induced by a visual suck.

These results demonstrate that EMG electrode position C was the most efficient with 58% of stimulation trains correctly pairing with visual sucks while maintaining good sensitivity to visual sucks. Using EMG in a closed-loop taVNS system is a safe and effective way to trigger taVNS stimuli in infants.

Example 2: Treating Neonates with Cranial Nerve Stimulation

In preterm infants with brain dysmaturation or term infants with hypoxic ischemic encephalopathy (HIE), feeding difficulty is the primary reason for delayed hospital discharge. Failure to achieve full oral feedings may be due to closure of critical developmental windows of neuroplasticity, or due to overt brain injury in HIE infants. Current therapies are limited to feeding by occupational or speech therapists once a day, and gastrostomy tube (g-tube) placement.

Figure 9:
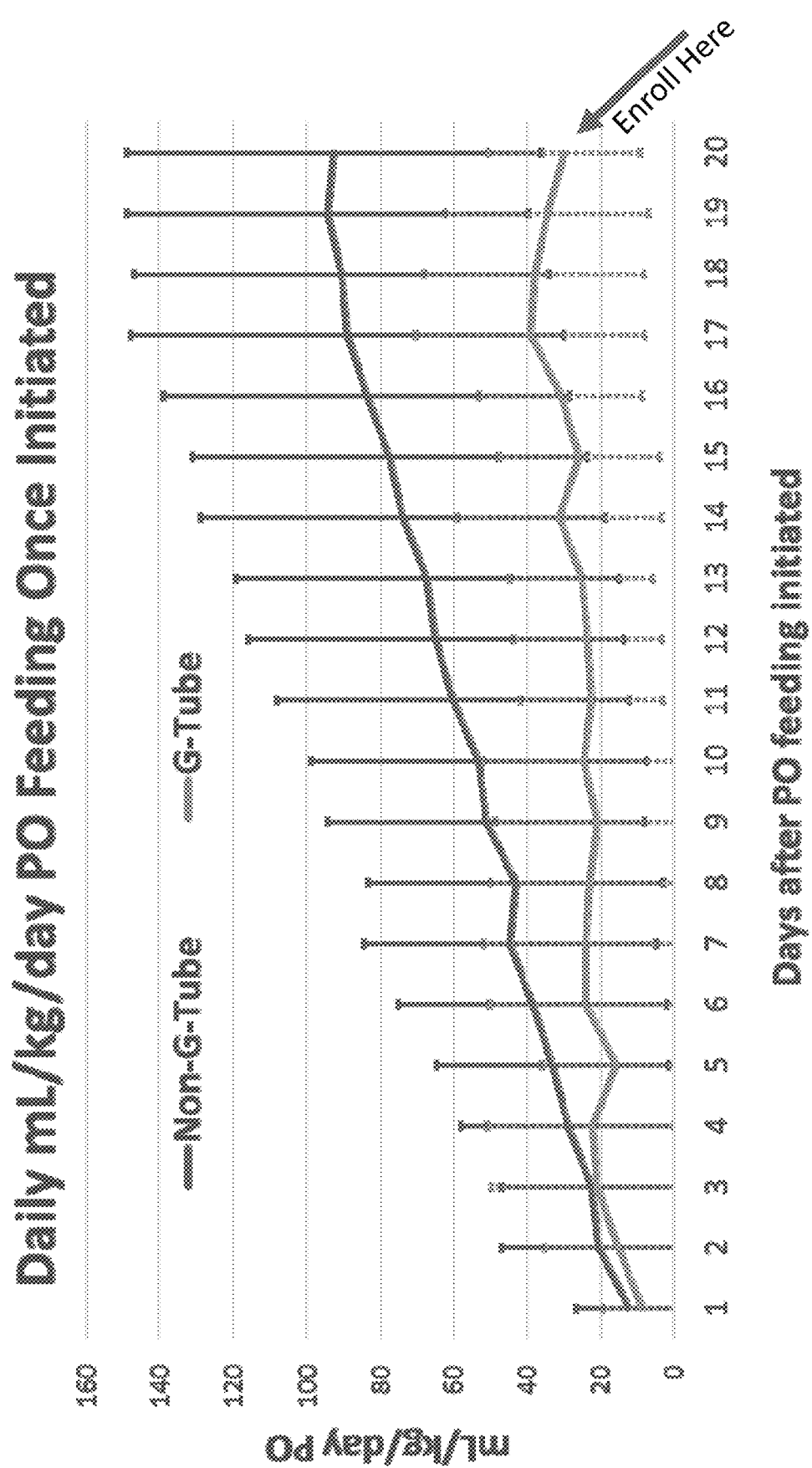
FIG. 9 depicts historical feeding data in a sample of infants having feeding difficulty.
Figure 10:
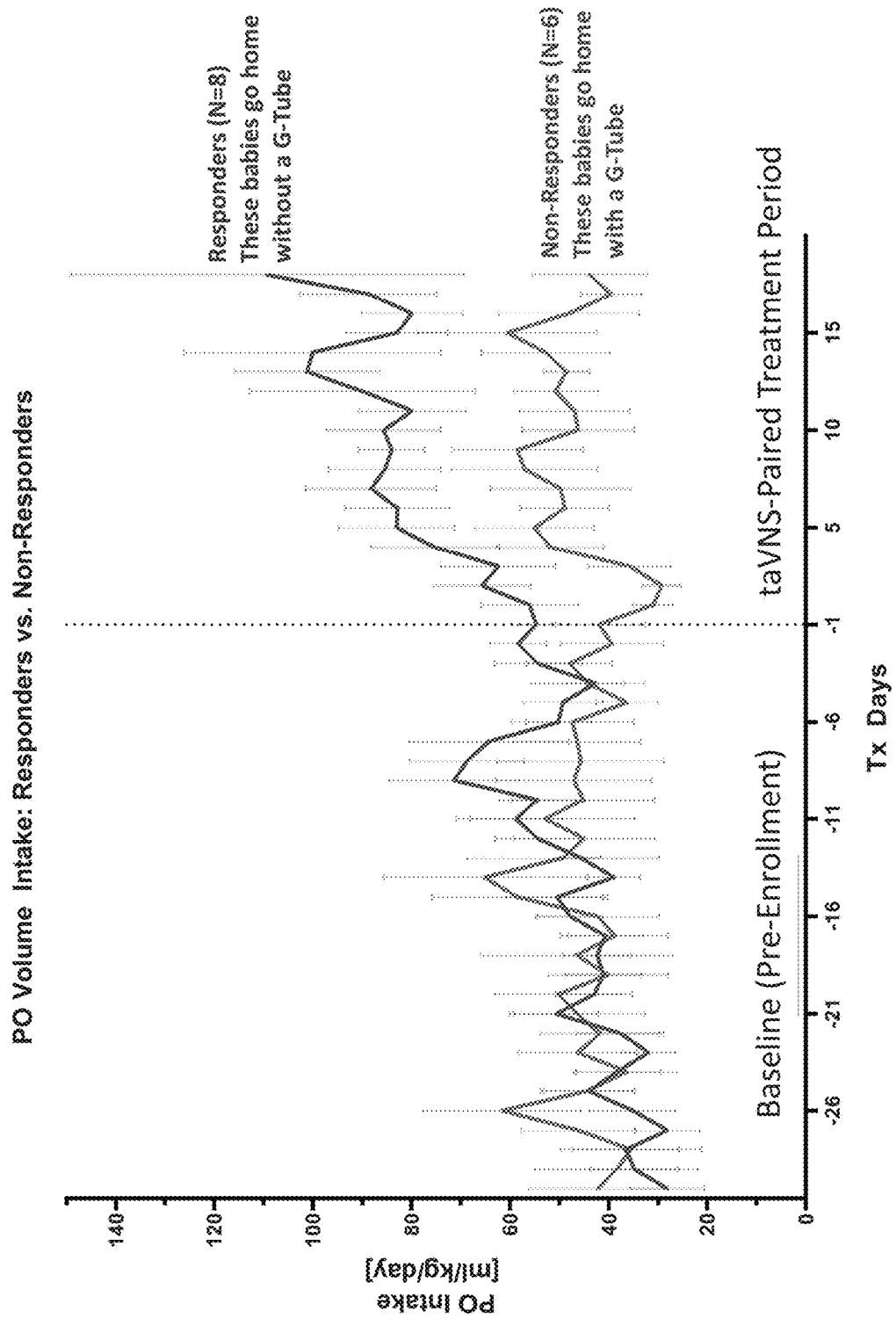
FIG. 10 depicts the results of administering cranial nerve therapy to 14 babies having feeding difficulty.

The present study monitored intake of infants 20 days post-oral (PO) feeding initiation. Infants that have failed feeding on average for 49 days were determined to be g-tube candidates and were enrolled in the cranial nerve stimulation trial (FIG. 9). 14 babies were analyzed in an interim analysis (FIG. 10). All babies were g-tube candidates and had been attempting to feed orally for an average of 49 days before enrollment. Treatment was administered based on previous protocols (stimulation delivered using a left ear electrode at 0.1 mA below perceptual threshold, 25 Hz frequency, 500 μs pulse width, for a 3.5 second train). 57% of the babies (8 of 14) reached the adequate PO intake (full feeds orally) that is clinically required to be discharged without a g-tube. The results demonstrate that in more than half of babies, cranial nerve stimulation facilitates their rehabilitation, enhances neuroplasticity, and facilitates motor learning.

Figure 11:
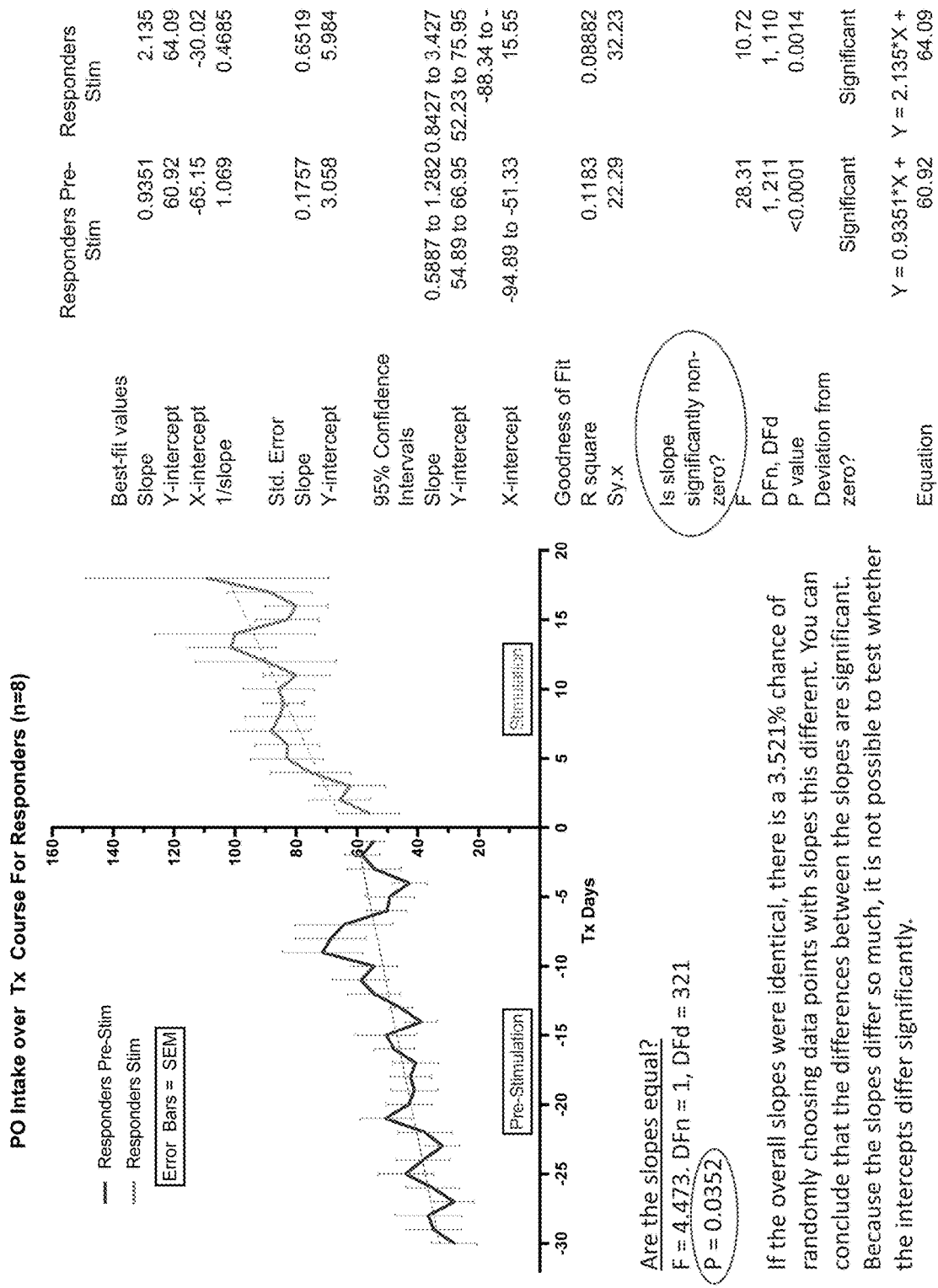
FIG. 11 depicts the results of statistical analysis for the 8 responders in the treatment group shown in FIG. 10; the responders have significant changes in their oral feeding behavior, indicated by significant changes in the slopes of their linear regression lines.
Figure 12:
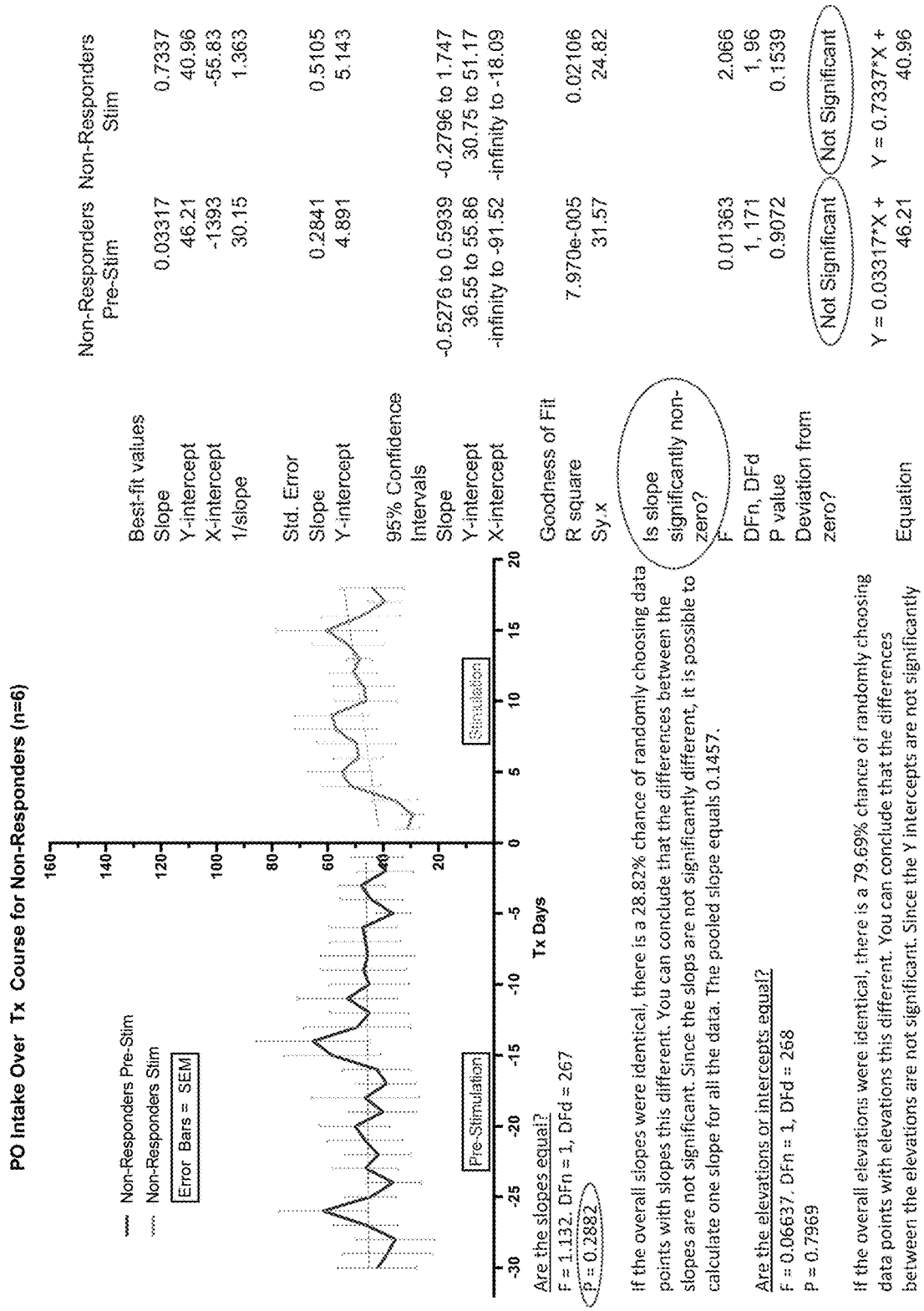
FIG. 12 depicts the results of statistical analysis for the 6 non-responders in the treatment group shown in FIG. 10; the non-responders have linear regression slopes that are non-significantly different from zero, indicating that no improvement has been achieved.

FIG. 11 and FIG. 12 depict the statistical analysis of the responder group and non-responder group. FIG. 11 shows that linear regression comparison of responders before and during stimulation treatment are significantly different, such that the slope increases after treatment. FIG. 12 shows that linear regression comparison of non-responders before and during stimulation treatment are not significantly different.

Figure 13A:
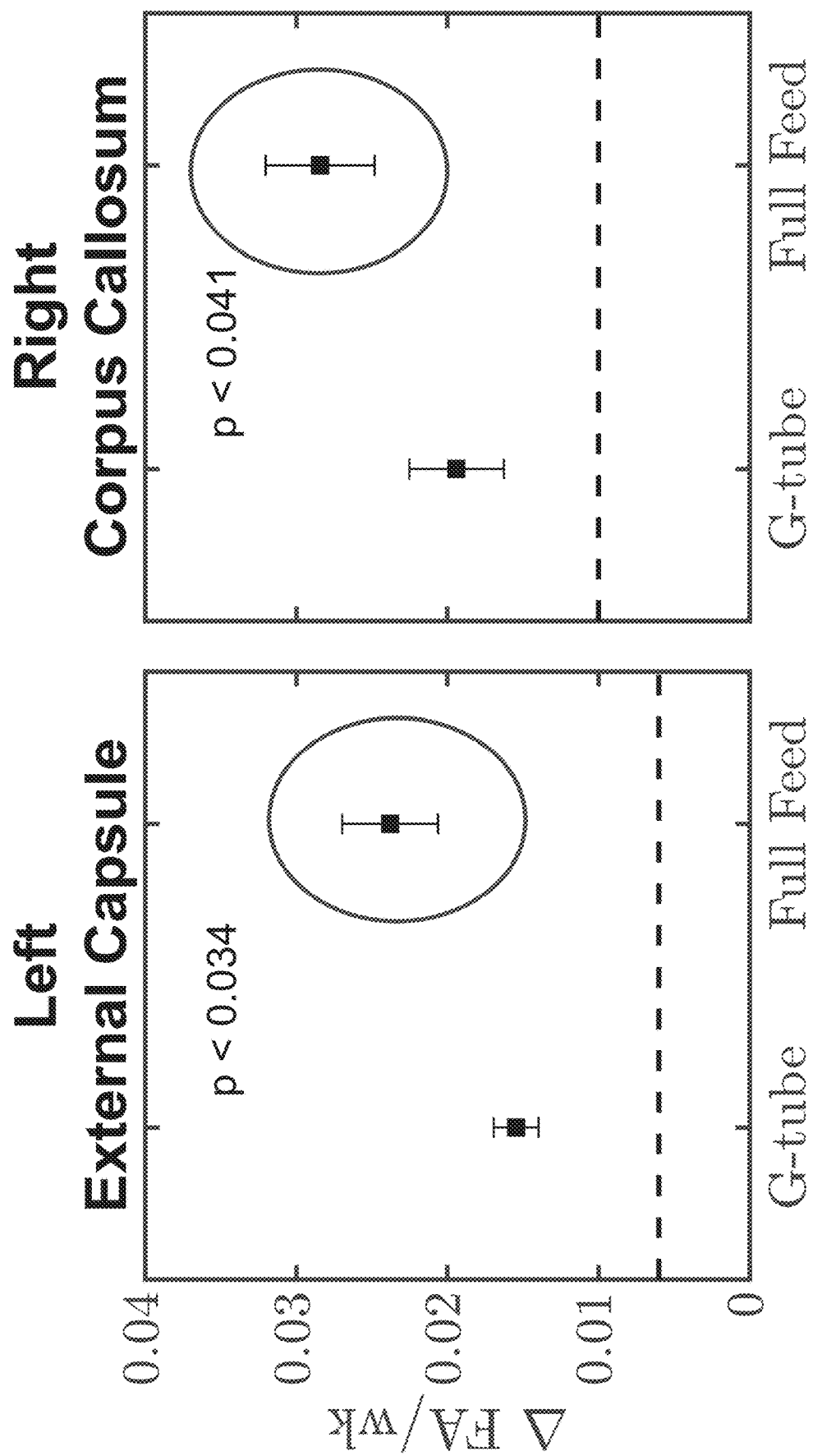
FIG. 13A and FIG. 13B depict the results of experiments investigating the effect of cranial nerve therapy on brain white matter tract integrity in infants.
Figure 13B:
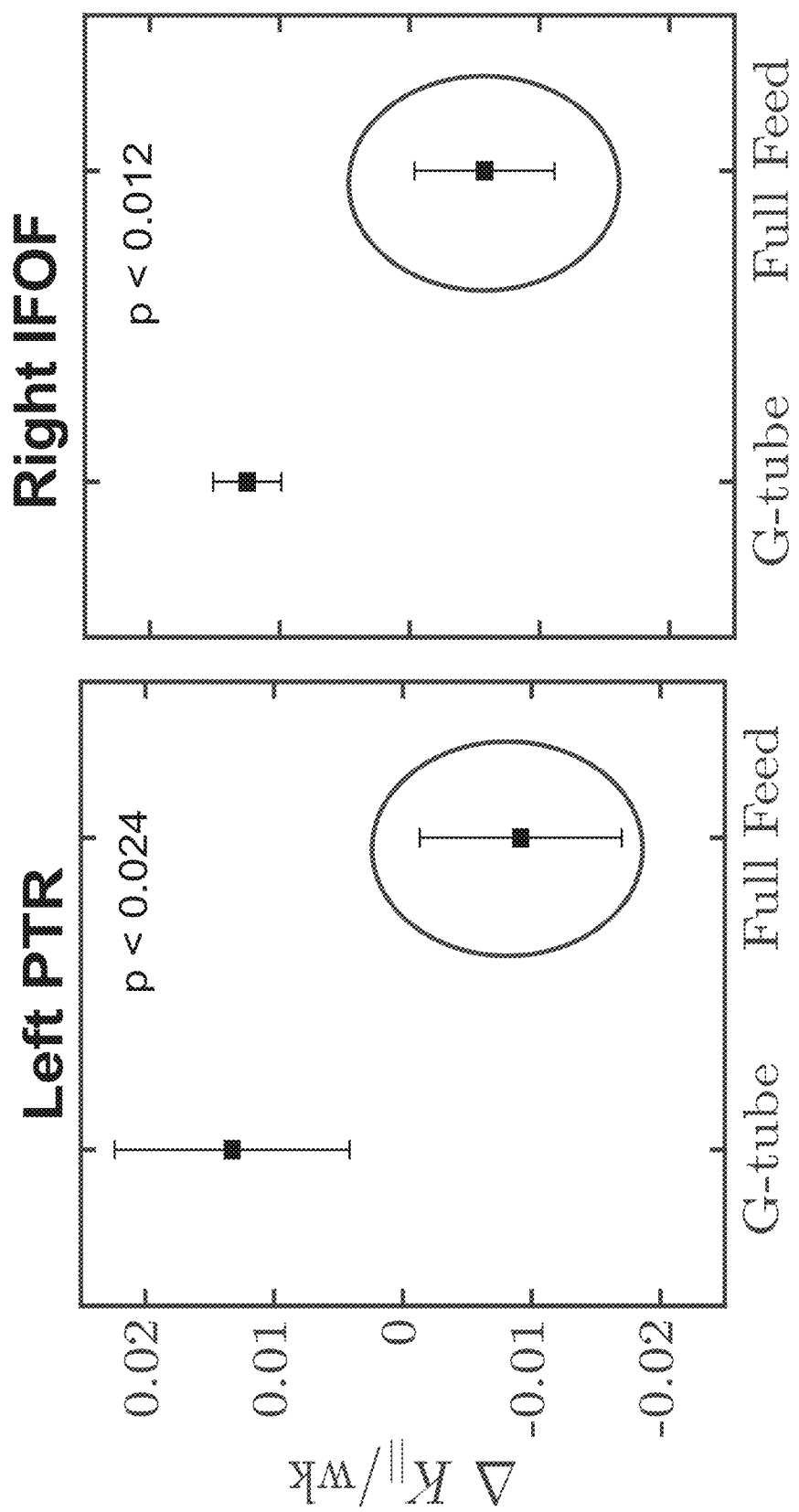

Treatment candidates were imaged to monitor the effects of treatment on brain development. Babies were scanned using MRI, treated for 2-4 weeks, and scanned again to investigate changes in white matter tracts. FIG. 13A and FIG. 13B demonstrate that cranial nerve stimulation had a greater effect on brain white matter tract integrity as indicated by fractional anisotropy (FA) and axial kurtosis ($K_{\parallel}$) in the responder group (full feed) than in the non-responder group (g-tube). Specific white matter tracts related to motor and sensorimotor integration were all strengthened. Furthermore, FA changes in both responder and non-responder groups were greater than expected with normal development (FIG. 13A), demonstrating that there is more inter-regional communication across the brain tract.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention.

What is claimed is:

1. A method of enhancing oromotor skills, comprising the steps of:
providing a nerve stimulation system comprising at least one sensor and at least one stimulating electrode;

securing the at least one stimulating electrode to a region of a subject's ear, and configured to stimulate a nerve of the subject;

providing the subject with a source of food;

measuring muscle activation using the at least one sensor; and administering stimulation using the at least one stimulating electrode to the nerve based on the measured muscle activation;

wherein the administered stimulation when paired with the consumption of the provided source of food enhances oromotor skills of the subject, wherein the oromotor skills comprise suckling.

2. The method of claim 1, wherein the nerve is selected from the group consisting of: the trigeminal nerve, the facial nerve, the accessory nerve, the hypoglossal nerve, the auricular branch of the vagus nerve, and the main bundle of the vagus nerve.

3. The method of claim 1, wherein the measuring step and the administering step are repeated in a closed loop.

4. The method of claim 1, wherein the at least one stimulating electrode is noninvasively secured to a subject's ear canal, tragus, cymba conchae, lobe, helix, anti-helix, or mastoid.

5. The method of claim 1, wherein the measured muscle activation surpasses a minimum threshold, wherein the minimum threshold is an absolute value selected from the group consisting of about: 0.1 µV, 0.5 µV, 1 µV, 5 µV, 10 µV, 50 µV, 100 µV, 200 µV, 300 µV, 400 µV, 500 µV, 1 mV, 5 mV, 10 mV, 20 mV, 30 mV, 40 mV, or 50 mV.

6. The method of claim 1, wherein the measured muscle activation surpasses a minimum threshold, wherein the minimum threshold is a change from a base measurement taken at rest selected from the group consisting of about: 0.1 µV, 0.5 µV, 1 µV, 5 µV, 10 µV, 50 µV, 100 µV, 200 µV, 300 µV, 400 µV, 500 µV, 1 mV, 5 mV, 10 mV, 20 mV, 30 mV, 40 mV, or 50 mV.

7. The method of claim 1, wherein the measured muscle activation surpasses a minimum threshold, wherein the minimum threshold is a percentage of a maximum potential of the muscle selected from the group consisting of: 1%, 2%, 3%, 4%, 5%, 10%, 15%, 20%, 25%, 30%, 35%, 40%, 45%, 50%, 55%, 60%, 65%, 70%, 75%, 80%, 85%, 90%, or 95%.

8. The method of claim 1, wherein the stimulation has an intensity selected from the group consisting of about: 0.01 mA, 0.05 mA, 0.1 mA, 0.2 mA, 0.3 mA, 0.4 mA, 0.5 mA, 0.6 mA, 0.7 mA, 0.8 mA, 0.9 mA, 1 mA, 1.5 mA, 2 mA, 2.5 mA, 3 mA, 3.5 mA, 4 mA. 4.5 mA, 5 mA. 6 mA, 7 mA, 8 mA, 9 mA, and 10 mA.

9. The method of claim 1, wherein the stimulation has a frequency selected from the group consisting of about: 1 Hz, 2 Hz, 3 Hz, 4 Hz, 5 Hz, 6 Hz, 7 Hz, 8 Hz, 9 Hz, 10 Hz, 15 Hz, 20 Hz, 25 Hz, 30 Hz, 35 Hz, 40 Hz, 45 Hz, and 50 Hz.

10. The method of claim 1, wherein the stimulation has a pulse width selected from the group consisting of about: 10 µs, 20 µs, 30 µs, 40 µs, 50 µs, 60 µs, 70 µs, 80 µs, 90 µs, 100 µs, 150 µs, 200 µs, 250 µs, 300 µs, 350 µs, 400 µs, 450 µs, 500 µs, 550 µs, 600 µs, 650 µs, 700 µs, 750 µs, 800 µs, 850 µs, 900 µs, 950 µs, and 1 ms.

11. The method of claim 1, wherein the stimulation has an on duration and an off duration, each selected from the group consisting of about: 0.1 seconds, 0.5 seconds, 1.5 seconds, 2 seconds, 2.5 seconds, 3 seconds, 3.5 seconds, 4 seconds, 4.5 seconds, 5 seconds, 10 seconds, 20 seconds, 30 seconds, 40 seconds, 50 seconds, 1 minute, 2 minutes, 3 minutes, 4 minutes, 5 minutes, 10 minutes, 15 minutes, 20 minutes, 30 minutes, 40 minutes, 45 minutes, 50 minutes, and 1 hour.

12. The system of claim 1, wherein the at least one sensor is selected from the group consisting of: a flow sensor, a pressure sensor, a suction sensor, a gyroscope, an accelerometer, a temperature sensor, and a volume sensor.

13. A cranial nerve stimulation system, comprising:
at least one sensor; and
at least one stimulating electrode configured to attach to a region of a subject's ear and adjacent to a nerve;
wherein the at least one stimulating electrode is electrically linked to the at least one sensor such that the at least one stimulating electrode is activated to stimulate the nerve when the at least one sensor detects muscle activation in at least one muscle, wherein the detected muscle activation relates to suckling of the subject.

14. The system of claim 13, wherein the at least one nerve is selected from the group consisting of: the trigeminal nerve, the facial nerve, the accessory nerve, the hypoglossal nerve, the auricular branch of the vagus nerve, and the main bundle of the vagus nerve.

15. The system of claim 13, further comprising a power source, a transmitter, and a processor communicatively connected to a non-transitory computer-readable memory with instructions store thereon, which when executed by the processor, initiates a closed-loop synchronization between activation and deactivation of the at least one stimulating electrode with the at least one sensor detecting muscle activation.

16. The system of claim 13, further comprising a wearable device with a power source, and a transmitter.

17. The system of claim 13, wherein the at least one sensor is selected from the group consisting of: a flow sensor, a pressure sensor, a suction sensor, a gyroscope, an accelerometer, a temperature sensor, and a volume sensor.

18. The system of claim 16, further comprising a bottle, a power source, a transmitter, and a processor communicatively connected to a non-transitory computer-readable memory with instructions store thereon, which when executed by the processor, synchronize activation and deactivation of the at least one stimulating electrode with the at least one sensor sensing feeding from the bottle and cessation of feeding from the bottle.

19. A method of enhancing muscle rehabilitation, comprising the steps of:
providing a nerve stimulation system comprising at least one sensor and at least one stimulating electrode;
securing the at least one stimulating electrode to a region of a subject's ear and to a subject's nerve;
measuring muscle group activation using the at least one sensor, wherein the muscle group activation relates to suckling of the subject; and
administering stimulation using the at least one stimulating electrode to the nerve based on measured muscle activity;
wherein the administered stimulation enhances muscle rehabilitation associated with the consumption of a source of food.

20. The method of claim 19, wherein the nerve is selected from the group consisting of: the trigeminal nerve, the facial nerve, the accessory nerve, the hypoglossal nerve, the auricular branch of the vagus nerve, and the main bundle of the vagus nerve.

21. The method of claim 19, wherein the measuring step and the administering step are repeated in a closed loop.

22. The method of claim 19, wherein the at least one sensor is selected from the group consisting of: a flow sensor, a pressure sensor, a suction sensor, a gyroscope, an accelerometer, a temperature sensor, and a volume sensor.

* * * * *